United States Patent [19]

Feldschuh

[11] Patent Number: 5,529,189
[45] Date of Patent: Jun. 25, 1996

[54] SYRINGE ASSEMBLY FOR QUANTITATIVE MEASUREMENT OF RADIOACTIVE INJECTATE AND KIT HAVING SAME

[75] Inventor: Joseph Feldschuh, Bronx, N.Y.

[73] Assignee: Daxor Corporation, New York, N.Y.

[21] Appl. No.: 510,374

[22] Filed: Aug. 2, 1995

[51] Int. Cl.⁶ .............. B65D 85/00; A61M 5/00; A61M 36/04
[52] U.S. Cl. .............. 206/570; 206/365; 600/4; 604/184; 604/198; 604/238; 604/263
[58] Field of Search .................... 206/365, 366, 206/370, 438, 570, 569; 600/4, 5; 604/183, 184, 186, 192, 198, 232, 236, 238, 248, 249, 263, 207

[56] References Cited

U.S. PATENT DOCUMENTS

| 1,234,582 | 7/1918 | Trueblood . |
| 1,279,069 | 9/1918 | Yoshida . |
| 1,589,882 | 6/1926 | Hein . |
| 2,642,868 | 6/1953 | Pontius . |
| 2,671,450 | 3/1954 | Dann . |
| 2,831,483 | 4/1958 | De Lorenzo . |
| 2,939,459 | 6/1960 | Lazarte et al. . |
| 3,089,491 | 5/1963 | Mirow . |
| 3,749,084 | 7/1973 | Cucchiara . |
| 3,911,916 | 10/1975 | Stevens . |
| 4,067,333 | 1/1978 | Reinhardt et al. . |
| 4,300,569 | 11/1981 | Bonneau . |
| 4,313,440 | 2/1982 | Ashley . |
| 4,364,376 | 12/1982 | Bigham . |
| 4,372,294 | 2/1983 | Strauss et al. . |
| 4,453,934 | 6/1984 | Gahwiler et al. . |
| 4,471,765 | 9/1984 | Strauss et al. . |
| 4,581,015 | 4/1986 | Alfano . |
| 4,643,721 | 2/1987 | Brunet . |
| 4,735,311 | 4/1988 | Lowe et al. . |
| 4,796,790 | 1/1989 | Hamilton ........................ 206/570 |
| 4,874,601 | 10/1989 | Flanagan . |
| 4,954,239 | 9/1990 | Mueller . |
| 5,002,538 | 3/1991 | Johnson . |
| 5,021,220 | 6/1991 | Mertens . |
| 5,024,231 | 6/1991 | Feldschuh et al. . |
| 5,117,981 | 6/1992 | Crawford et al. . |

Primary Examiner—Jimmy G. Foster
Attorney, Agent, or Firm—Amster, Rothstein & Ebenstein

[57] ABSTRACT

A disposable single-use kit for administering a precise dose of radioactive tracer to a subject with an accuracy of at least 99.9% by weight. The kit comprises a syringe, pre-filled with a known quantity of a radioactive tracer as injectate. The back of a small-bore needle is affixed to the syringe front. The front of a removable plastic needle cover incorporates airtight means for creating and maintaining an airlock in the needle front, thereby to prevent any contact between the tracer and the cover and so preclude any loss of tracer upon removal of the cover from the needle. A valve normally seals the syringe back, the valve including actuatable means for enabling a fluid flow into the syringe back, both for pre-filling of the syringe with injectate and for flushing of the injectate from the syringe into the subject.

11 Claims, 2 Drawing Sheets

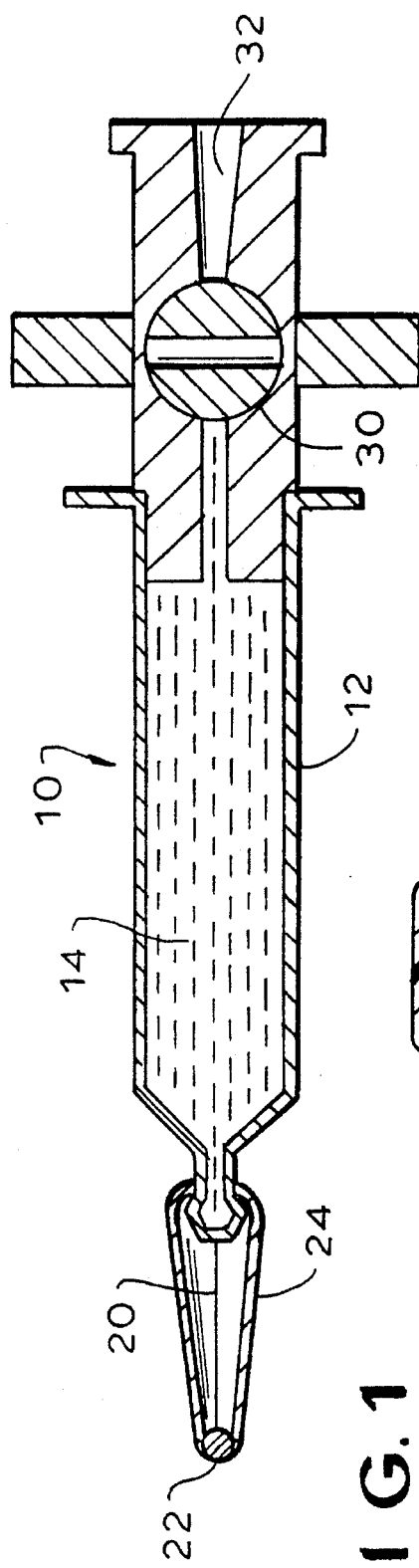
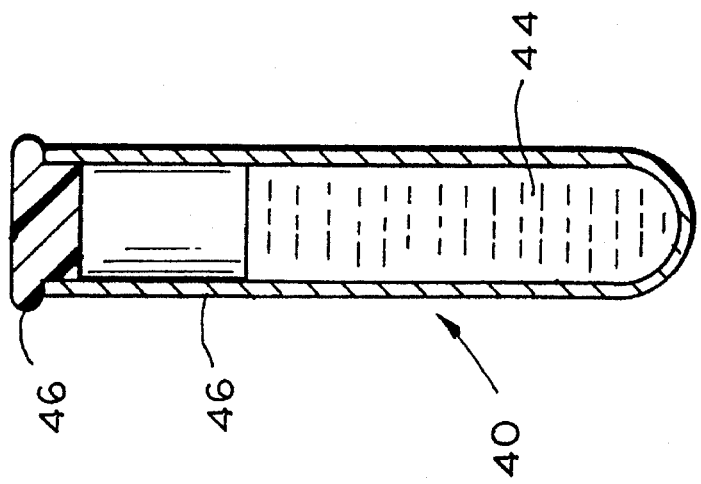
FIG. 1
FIG. 2

SYRINGE ASSEMBLY FOR QUANTITATIVE MEASUREMENT OF RADIOACTIVE INJECTATE AND KIT HAVING SAME

BACKGROUND OF THE INVENTION

The present invention relates to a syringe assembly for the quantitative dilution measurement of radioactive injectate and a kit having the same, and more particularly to such an assembly which delivers the injectate with a high precision.

The kit of the present invention facilitates the performance of quantitative radioactivity dilution measurements, such as that performed by the Automated Multi-Point Blood Volume Analyzer described in U.S. Pat. No. 5.02444,231. In such measurements, a precise amount of radioactive tracer is administered to the subject. After dilution of the tracer has occurred, the radioactivity of a sample or samples from the subject is compared to that of a standard prepared from the original injectate. This standard is prepared by diluting an equivalent dose of radiation into a known volume. In the prior art, a technician would prepare the standards manually at the time of the procedure. This has several disadvantages compared with the use of the kit described herein. It is time consuming, subject to technician error, and requires access to a lab with appropriate glassware. It requires handling of a supply of radioactive tracer; and such a supply is likely to have a level of activity many times higher than that contained in a single-use kit, as it is not commercially practical to order radioisotopes in very small amounts.

Various U.S. patents have been issued for kits involving radioactivity, but they all have in common that they are designed to facilitate qualitative studies. For the purposes of the present invention, a qualitative injection is one where a precision of 97% or 98% is sufficient, as is generally the case with a therapeutic injection, or one where a tracer compound is used for imaging purposes. By contrast, a quantitative injection is one where the injectate must be delivered with high precision, at least 99.9% of an expected dose, typically because the subsequent dilution or uptake of the injectate by the subject is used to precisely calculate some numerical value, such as the volume of blood in the subject into which the injectate is diluted (i.e., injected).

U.S. Pat. No. 4,364,376 describes a device for injecting a radioactive bolus into a body. The prior art for a quantitative dilution measurement (the object of the present invention) is similar to the prior art as described therein, with a few changes which reflect the need for a higher degree of precision. Thus, the standard 1 cc syringe would be replaced by a calibrated syringe capable of delivering a precise amount of fluid, and this same calibrated syringe would be used to prepare a plurality of standards by diluting an equivalent injectate into a known volume. By comparing the level of tracer in the standards with the level of tracer in samples taken from the subject, the unknown volume of the subject can be determined. The patented device is an improvement on the prior art qualitative applications for which it was designed, such as imaging, these applications typically using relatively high doses of radiation, and hence justifying the emphasis on improved shielding. Despite its suggestion of a "flow-through" feature, the patented device is inadequate, however, to the task of quantitative dilution measurement because the process of filling the syringe with the injectate through the needle (see FIGS. 3 and 4) is subject to an inherent mechanical variability on the order of 2% or 3%, as well as to technician error.

Each of U.S. Pat. No. 2,671,450, U.S. Pat. No. 4,735,311 and U.S. Pat. No. 2,831,483 discloses an air-lock design. The use of an air-lock mechanism allows the syringe to be pre-filled from the back, thereby avoiding the problem of leakage from the needle. The possibility for technician error is also decreased, as the technician needs only to perform the injection step.

Other patents which deal with radioactivity are only tangentially relevant. U.S. Pat. No. 4,300,569 describes a procedure for radiolabelling red blood cells, as do U.S. Pat. No. 4,471,765 and U.S. Pat. No. 4,372,294. However, the devices disclosed therein are not concerned with delivering a calibrated dosage of an already-labelled blood component (e.g., albumin I-131) in a quantitative study. Thus the disclosed devices lack a "flow-through" design. Even if the apparatus is flushed with a sterile saline solution, there will still inevitably be incomplete delivery of the radioisotope due to the use of the mixing syringes. U.S. Pat. No. 4,874,601 and U.S. Pat. No. 5,021,220 describe kits for producing radiolabelled organic compounds of pharmaceutical purity (such as albumin I-131), but they do not disclose devices for delivering the same quantitatively. U.S. Pat. No. 4,954,239 describes a disposable kit for irrigating an IV line, but not for the quantitative delivery of a calibrated dosage of radioactive tracer. As the syringes described above cannot be washed or "flushed" out, some of the injectate will remain in the volume of the needle and in the syringe. This is adequate for the therapeutic or qualitative diagnostic purposes for which they were designed, but not for the quantitative purpose for which the present kit is designed. Other designs for disposable syringes, such as those disclosed in U.S. Pat. No. 1,589,882, U.S. Pat. No. 2,642,868 and U.S. Pat. No. 3,089,491, share this limitation.

The prior art for syringe design is quite extensive, but nowhere is the combination of the needle air-lock feature and the flow-through mechanism feature found in the context of a quantitative dilution measurement of radioactivity, the combination of these two features in a single syringe design enabling a new function for a disposable syringe—namely, that of quantitative analysis.

Accordingly, an object of the present invention is to provide a syringe assembly combining an air-lock feature and a flow-through mechanism feature.

Another object is to provide such an assembly which enables the syringe assembly to be used for quantitative analysis in the context of a quantitative dilution measurement of radioactivity.

A further object is to provide in one embodiment a disposable kit for delivery of a precise dose of radioactive tracer to a subject with an accuracy of at least 99.9% by weight.

SUMMARY OF THE INVENTION

The present invention comprises a kit containing the essential items used to perform a measurement of radioactive tracer dilution in a living subject. In a preferred embodiment, this kit contained I-131 serum albumin and is used to measure human blood volume in conjunction with the Automated Multi-Point Blood Volume Analyzer described in U.S. Pat. No. 5.02444,231. The kit can also be used to measure human blood volume in the absence of the analyzer, if the user has access to a gamma counter and is willing to perform the necessary calculations manually.

The kit described herein has two main features: (i) the provision of a shippable, disposable, ready-to-use injectate syringe assembly capable of delivering a precisely measured amount of a compound through the novel combination of a needle air-lock and a flow-through mechanism, and (ii) the provision of a complete kit for performing a quantitative dilution analysis, with a ready-to-use injectate and ready-to-use, already calibrated standards. The combination of the air-lock and the "flow-through" mechanism insures that the entire dose of injectate is administered, to at least a 99.9% by weight accuracy.

The tracer is introduced to the subject by flushing the syringe with sterile saline through the valve at the back end of the syringe. The radioactivity of samples taken subsequently from the subject is compared quantitatively with that of the standards provided with the kits, and can be used to calculate such quantities as plasma volume, total blood volume, rates of circulatory leakage, etc. The kit optionally includes a syringe containing sterile saline solution for use in flushing the injectate into the subject as described above, as well as other items designed to expedite the performance of a specific procedure such as instructions, a worksheet for recording data required in the calculations, blank test tubes of appropriate size, and adhesive labels.

More particularly, the present invention is a disposable single-use kit for administering a precise dose of radioactive tracer to a subject with an accuracy of at least 99.9% by weight. The kit comprises a syringe having a front and a back, the syringe being pre-filled with a known quantity of a radioactive tracer as injectate. A small-bore needle has a front and a back, the needle back being affixed to the syringe front. A removable plastic needle cover has a front and a back, the cover front incorporating airtight means for creating and maintaining an airlock in the needle front, thereby to prevent any contact between the tracer and the cover and preclude any loss of tracer upon removal of the cover from the needle. A valve normally seals the syringe back, the valve including actuatable means for enabling a fluid flow into the syringe back.

In a preferred embodiment, the needle cover incorporates adjacent to the cover front a rubber stopper which acts as the airtight means and receives the needle front to maintain an airlock within the needle, thereby to prevent any contact between the tracer and the stopper and preclude any loss of the tracer upon removal of the stopper from the needle front.

In the preferred embodiment, the valve has a front, a back and a bore connecting the valve front and the valve back, the valve being movable between a flow-through orientation enabling a fluid flow through the bore into the syringe (e.g., for pre-filling with injectate or flushing with fluid) and a blocking orientation precluding a fluid flow into the syringe. The bore is sized to accept at the end thereof adjacent the valve back a standard syringe or IV tubing. Finally, the syringe is pre-filled with the tracer via the valve, and not via the needle, and is adapted to be flushed with a flow of flush fluid introduced via the valve.

The present invention further encompasses a kit wherein the syringe is pre-filled, sterilized and sealed, and packaged into the kit, together with a plurality of calibrated standards, each calibrated standard consisting of an aliquot of an equivalent dose of radioactive tracer diluted into a known volume.

BRIEF DESCRIPTION OF THE DRAWING

The above and related objects, feature advantages of the present invention will be more fully understood by reference to the following detailed description of the presently preferred, albeit illustrative, embodiment of the present invention when taken in conjunction with the accompanying drawing wherein:

FIG. 1 is a schematic cross section of the pre-filled injectate syringe assembly;

FIG. 2 is a schematic cross section of a standard; and

DETAILED DESCRIPTION OF THE PREFERRED EMBODIMENTS

Figure 3:
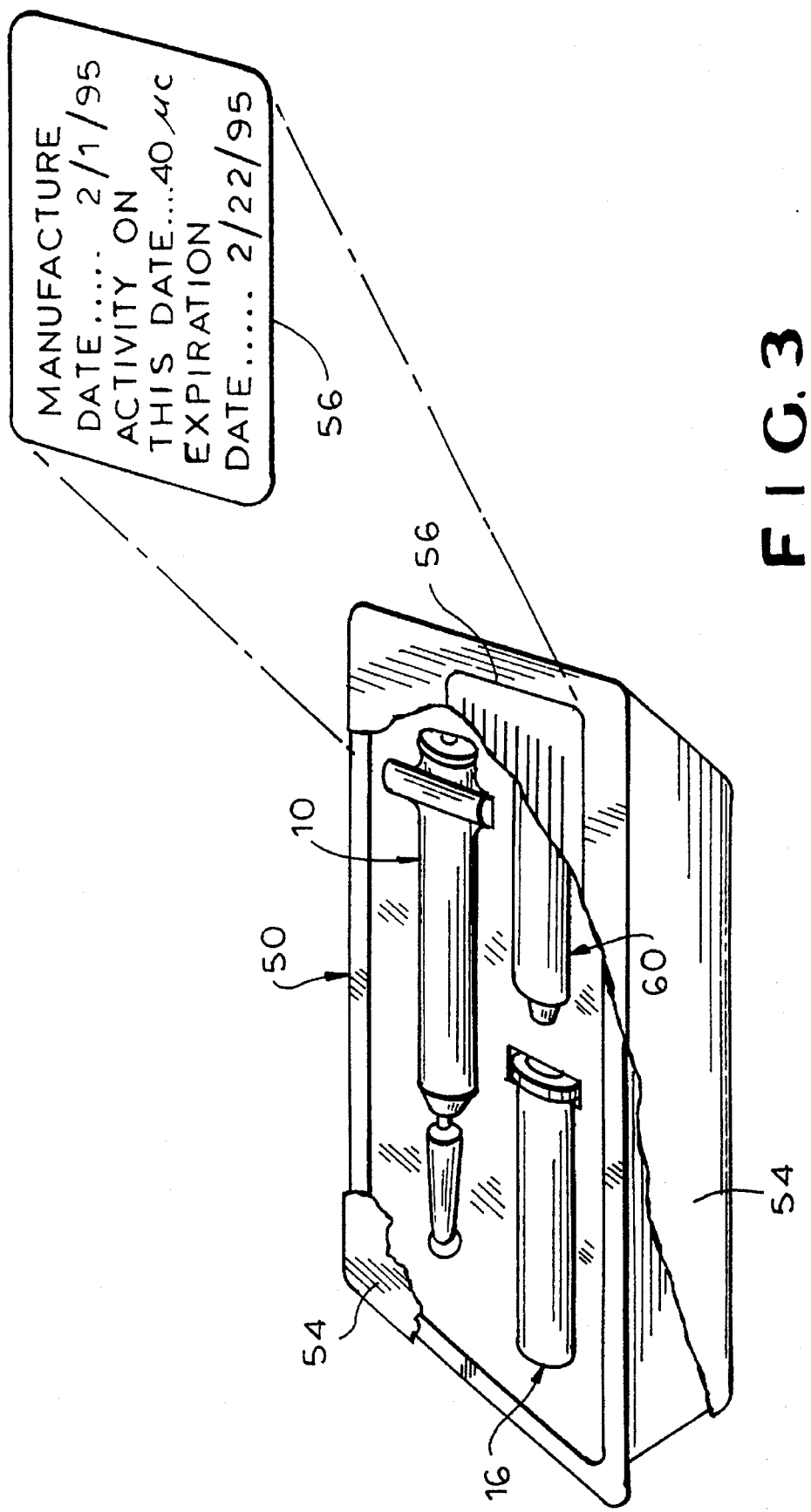
FIG. 3 is an isometric view of the injectate syringe assembly and the standards packaged together for shipping, with portions thereof removed to reveal details of internal construction.

Referring now to the drawing, and in particular to FIG. 1 thereof, therein illustrated is a syringe assembly according to the present invention generally designated by the reference numeral 10. The syringe 12 is filled with a radioactive injectate 14, for example, 1 ml of I-131 serum albumin having an activity of between 5 and 40 microcuries. The front end of the syringe 12 is sealed with a conventional small bore needle 20, which penetrates an airtight stopper 22, preferably formed of rubber, which is integrated into the plastic needle cover 24. The back end of the syringe 12 is sealed with a valve or two-way stopcock 30, illustrated in the closed position. The rear end of the valve 30 has an opening 32 which accepts a standard syringe or standard IV tubing infusion set.

The components are prepared in the following manner: The empty syringe assembly 10 is held in the vertical position, with the valve 30 in the open position and the front of the needle 20 in stopper 22 of the needle cover 24. The syringe 12 is then filled with injectate from the back through open valve 30 using a second calibrated syringe, e.g., one which can be set mechanically to produce a repeatable motion of the piston, and hence reproduce identical volumes to a precision of at least 99.9% by weight. The valve 30 is then closed. The syringe assembly 10 is then sealed in plastic, and sterilized.

An airlock provided by the air in the needle 20 (intermediate the stopper 22 and the tracer 14) insures that no tracer 14 is lost when the needle cover 24 and its integral stopper 22 are removed. The air lock provided by a 22 gauge needle is sufficient to withstand accelerations of 200 G in a centrifuge, so it should certainly remain in place during normal shipping and handling.

Referring now to FIG. 2 in particular, the sealed calibrated standard, generally designated 40, consists of a container 42 filled with the standard solution 44 and sealed with a leak-proof cap 46. The standards are produced by using the same calibrated syringe and the same tracer source as used in pre-filling the injectate syringe, and injecting an identical volume of injectate into a volumetric flask (e.g., 1000 ml). The flask is then filled with a sterile saline solution, and the contents are mixed. Another calibrated syringe or pipette is used to extract 1.00 ml samples of the resulting aliquot, which are placed in suitable containers and sealed.

Referring now to FIG. 3 in particular, therein illustrated is the dated radioactive tracer kit of the present invention, generally designated 50 and containing the injectate syringe assembly 10 and the standards 16 packaged together for shipping in a molded container 52. The package is sealed with a plastic wrapper 54. Any shielding necessary to comply with standard radiation handling protocols would be placed outside the wrapper 54. Affixed to the wrapper is a label 56, containing information including the date of manufacture, the radioactivity present in the injectate at that time, an expiration date based on the half-life of the tracer, and the required level of activity for the clinical test. In the case of labelled compounds which degrade themselves, this expiration date may reflect the decay of the tagged molecule itself. For example, the half life of I-131 is approximately 8 days, so, if the kit is manufactured with an activity level of 40 microcuries, then the expiration date would be specified as 21 days after the manufacture date, which is the limit of usability of the albumin, even though the activity level of the injectate would fall within 5 and 40 microcuries for a full 24 days (3 half-lives). Note that the information about the activity level of the injectate is useful because with it the technician can choose an appropriate amount of time to count each sample to achieve a desired level of accuracy (e.g., 10,000 counts per specimen).

During use, the needle cover 24 is removed from the injectate syringe needle 20, which is then inserted into a running IV or a vein of the subject. A second syringe or IV tubing containing sterile saline solution is connected to the stopcock 30 at the back of the injectate syringe 12, and the stopcock 30 between them is opened. The injectate 14 is then flushed into the subject with a washout of at least 99.9% by weight.

The radioactivity of samples taken subsequently from the subject is compared quantitatively with that of the standards 16 provided with the kits, and can be used to calculate such quantities as plasma volume, total blood volume, rates of circulatory leakage, etc.

The kit optionally includes a syringe, generally designated 60 and containing sterile saline solution for use in flushing the injectate into the subject as described above, as well as other items designed to expedite the performance of a specific procedure such as instructions, a worksheet for recording data required in the calculations, blank test tubes of appropriate size, and adhesive labels.

To summarize, the present invention provides a syringe assembly combining an air-lock feature and a flow-through mechanism feature so that the syringe assembly may be used for quantitative analysis in the context of a quantitative dilution measurement of radioactivity. The present invention also provides in one embodiment a disposable kit for delivery of a precise dose of radioactive tracer to a subject with an accuracy of a least 99.9% by weight.

Now that the preferred embodiments of the present invention have been shown and described in detail, various modifications and improvement thereon will readily become apparent to those skilled in the art. Accordingly, the spirit and scope of the present invention is to be construed broadly and limited only by the appended claims, and not by the foregoing specification.

I claim:

1. A disposable single-use kit for administering a precise dose of radioactive tracer to a subject with an accuracy of at least 99.9% by weight, said kit comprising:

(A) a syringe having a front and a back, said syringe being pre-filled with a known quantity of a radioactive tracer as injectate;

(B) a small-bore needle having a front and a back, said needle back being affixed to said syringe front;

(C) a removable plastic needle cover having a front and a back, said cover front incorporating airtight means for creating and maintaining an airlock in said needle front, thereby to prevent any contact between the tracer and said cover and preclude any loss of tracer upon removal of said cover from said needle; and (D) a valve normally sealing said syringe back, said valve including actuatable means for enabling a fluid flow into said syringe back.

2. The kit of claim 1 wherein said needle cover incorporates adjacent to said cover front a rubber stopper which acts as the airtight means and receives said needle front to maintain an airlock within said needle, thereby to prevent any contact between the tracer and said stopper and preclude any loss of the tracer upon removal of said stopper from said needle front.

3. The kit of claim 1 wherein said syringe is pre-filled with the tracer via said valve and not via said needle.

4. The kit of claim 3 wherein said syringe is adapted to be flushed with a flow of flush fluid introduced via said valve.

5. The kit of claim 1 wherein said valve has a front, a back and a bore connecting said valve front and said valve back, said valve being movable between a flow-through orientation enabling a fluid flow through said bore into said syringe and a blocking orientation precluding a fluid flow into said syringe.

6. The kit of claim 5 wherein said syringe is pre-filled with the tracer via said valve and not via said needle.

7. The kit of claim 6 wherein said syringe is adapted to be flushed with a flow of flush fluid introduced via said valve.

8. The kit of claim 5 wherein said bore is sized to accept at the end thereof adjacent said valve back a standard syringe or IV tubing.

9. The kit of claim 1 wherein said syringe is pre-filled, sterilized and sealed, and packaged into said kit, together with a plurality of calibrated standards, each said calibrated standard consisting of an aliquot of an equivalent dose of radioactive tracer diluted into a known volume.

10. A disposable single-use kit for administering a precise dose of radioactive tracer to a subject with an accuracy of at least 99.9% by weight, said kit comprising:

(A) a syringe having a front and a back, said syringe being pre-filled with a known quantity of a radioactive tracer as injectate;

(B) a small-bore needle having a front and a back, said needle back being affixed to said syringe front;

(C) a removable plastic needle cover having a front and a back, said cover front incorporating an airtight rubber stopper which receives said needle front for creating and maintaining an airlock in said needle front, thereby to prevent any contact between the tracer and said stopper and preclude any loss of the tracer upon removal of said stopper from said needle front; and (D) a valve normally sealing said syringe back, said valve including actuatable means for enabling a fluid flow into said syringe back, said valve having a front, a back and a bore connecting said valve front and said valve back, said valve being movable between a flow-through orientation enabling a fluid flow through said bore into said syringe and a blocking orientation precluding a fluid flow into said syringe;

whereby, when said syringe is pre-filled with a precise dose of the tracer via said valve and said syringe is flushed with a flow of flush fluid introduced via said valve, said tracer is administered to a subject with an accuracy of at least 99.9% by weight.

11. The kit of claim 10 wherein said syringe is pre-filled, sterilized and sealed, and packaged into said kit, together with a plurality of calibrated standards, each said calibrated standard consisting of an aliquot of an equivalent dose of radioactive tracer diluted into a known volume.

* * * * *